(12) United States Patent
Poncet et al.

(10) Patent No.: US 12,419,761 B2
(45) Date of Patent: Sep. 23, 2025

(54) SYSTEM AND METHOD FOR VERIFICATION OF LOCATION DURING SURGERY

(71) Applicant: DEPUY IRELAND UNLIMITED COMPANY, County Cork (IE)

(72) Inventors: Didier Poncet, Villeurbanne (FR); Nicolas Demanget, Saint-Egreve (FR)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 422 days.

(21) Appl. No.: 17/815,458

(22) Filed: Jul. 27, 2022

(65) Prior Publication Data

US 2023/0072142 A1 Mar. 9, 2023

Related U.S. Application Data

(60) Provisional application No. 63/240,665, filed on Sep. 3, 2021.

(51) Int. Cl.
*A61F 2/46* (2006.01)
*A61F 2/40* (2006.01)

(52) U.S. Cl.
CPC .............. *A61F 2/4657* (2013.01); *A61F 2/40* (2013.01); *A61F 2002/4658* (2013.01); *A61F 2002/4668* (2013.01)

(58) Field of Classification Search
CPC .. A61F 2/4657; A61F 2/40; A61F 2002/4658; A61F 2002/4668
USPC ....................................................... 606/102
See application file for complete search history.

(56) References Cited

U.S. PATENT DOCUMENTS

| 8,382,765 | B2 | 2/2013 | Axelson |
| 8,469,965 | B2 | 6/2013 | Neubauer |
| 9,987,092 | B2 | 6/2018 | Hladio |
| 10,136,950 | B2 | 11/2018 | Schoenefeld |
| 2003/0209096 | A1* | 11/2003 | Pandey ................ A61B 90/36 73/865.9 |
| 2005/0234332 | A1 | 10/2005 | Murphy |
| 2007/0167741 | A1* | 7/2007 | Sherman ............... A61B 90/36 600/424 |
| 2016/0175055 | A1 | 6/2016 | Hook |

(Continued)

FOREIGN PATENT DOCUMENTS

| EP | 2248484 B1 | 7/2011 |
| EP | 3035880 A1 | 5/2016 |

(Continued)

OTHER PUBLICATIONS

International Search Report and Written Opinion for PCT/EP2022/074342 mailed on Dec. 8, 2022.

(Continued)

*Primary Examiner* — Kevin T Truong
*Assistant Examiner* — Diana Jones
(74) *Attorney, Agent, or Firm* — Kramer & Amado, P.C.

(57) ABSTRACT

A verification instrument configured to verify the location of a surgical end-effector, including: a body; a navigation element disposed and configured to represent a spatial location of the body; a first clip extending from the body configured to clip onto a tool; a length measurement portion disposed at a first angle from the body, wherein the length measurement portion is configured to contact a tool tip when the first clip is clipped onto the tool.

20 Claims, 13 Drawing Sheets

(56) References Cited

U.S. PATENT DOCUMENTS

2016/0255823 A1* 9/2016 Thomas ................. A01K 97/10
2018/0338799 A1* 11/2018 Hladio ................. A61B 5/4851

FOREIGN PATENT DOCUMENTS

WO    WO-2016141378 A1 * 9/2016 ............. A61B 34/20
WO    2021/059253 A2    4/2021
WO    2021/084484 A2    5/2021

OTHER PUBLICATIONS

Anonymous, "Brainlab Hip Instrument User Guide 1.1", Dec. 31, 2015, pp. 1-110, https://www.brainlab.com/wp-content/uploads/2016/12/Hip-Instrument-User-Guide.pdf.

Seattle Science Foundation, "MIS Navigation: Step by Step—Terrance Kim, MD", Mar. 9, 2020, https://www.youtube.com/watch?v=zGcUn36-1FM.

Anonymous, "Software User Guide Rev. 1.0 Kolibri cranial/ENT Ver. 2.7", Jan. 1, 2010, https://www.manualslib.com/manual/1863481/Brainlab-Kolibri-Cranial.html.

* cited by examiner

SYSTEM AND METHOD FOR VERIFICATION OF LOCATION DURING SURGERY

CROSS-REFERENCE TO RELATED APPLICATIONS

This application claims benefit to U.S. Provisional Patent Application No. 63/240,665 filed on Sep. 3, 2022, the contents of which are hereby incorporated by reference for all purposes as if fully set forth herein.

TECHNICAL FIELD

Various exemplary embodiments disclosed herein relate generally to a system and method for verification of location during surgery.

BACKGROUND

Various surgical instruments, systems, and methods for tracking or navigating surgical instruments relative to portions of patient anatomy during a procedure have been developed. Such instruments, systems, and methods can be used in various procedures, including, e.g., robotic or robot-assisted orthopedic surgical procedures such as total shoulder arthroplasty, knee arthroplasty, spinal fusion surgery, etc.

Many different surgical procedures utilize some form of surgical navigation or tracking to aid in positioning surgical instruments relative to portions of patient anatomy during a procedure. One such type of procedure is robotic or robot-assisted surgical procedures, where surgical navigation can be important to correctly position a robotically controlled or assisted surgical instrument relative to a patient. Further details of exemplary surgical systems that can utilize surgical navigation can be found in International Publication Nos. WO 2018/103945; WO 2018/104523; WO 2018/167246; WO 2018/104439; and U.S. Pat. Pub. No. 2016/0135816. The entirety of each of these publications is incorporated by reference herein for all purposes.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a verification instrument configured to verify the location of a surgical end-effector, including: a body; a navigation element disposed and configured to represent a spatial location of the body; a first clip extending from the body configured to clip onto a tool; and a length measurement portion disposed at a first angle from the body, wherein the length measurement portion is configured to contact a tool tip when the first clip is clipped onto the tool.

Various embodiments are described, further comprising a resection measurement portion connected to the connector at a second predetermined angle from the body.

Various embodiments are described, further comprising a second clip extending from the body, where the first clip and second clip include colinear openings.

Various embodiments are described, wherein the body further comprises a second extension extending from the body, a first navigation element of the three navigation elements is located at a distal end of the first extension, and a second navigation element of the three navigation elements is located at a distal end of the second extension.

Various embodiments are described, wherein the first angle is substantially 90 degrees.

Various embodiments are described, wherein the first clip includes: a first arm with a gripping surface configured to grip a cylindrical portion of the end-effector; and a second arm with a gripping surface configured to grip the cylindrical portion of the end-effector.

Various embodiments are described, wherein the first clip comprises a slot in the gripping surface configured to grip a flat portion of the end-effector.

Various embodiments are described, wherein the first arm and the second arm have a textured exterior surface.

Further various embodiments relate to a method of verifying the location of an end-effector relative to a handpiece with a navigation device using a verification instrument, including: attaching a first clip of the verification instrument to the end-effector so that an end of the end-effector contacts a length measurement portion of the verification instrument; initiating a measurement of the location of the verification instrument and the navigation device and verification of the location of the end-effector relative to the navigation array using a navigation system; removing the verification instrument from the end-effector; and tracking of the end-effector using the navigation system.

Various embodiments are described, including: determining the length of the end-effector and an identification of the type of end-effector connected to the handpiece using a navigation system; and indicating to a user of the verification instrument the identification of the end-effector attached to the handpiece using the navigation system.

Further various embodiments relate to a method of determining an angle of a resection surface of a bone using a verification instrument including a navigation device and a resection measurement portion, including: placing a resection measurement surface of a resection measurement portion on the resection surface of the bone; initiating a measurement of the location of the verification instrument relative to the navigation device and determining an angle of the resection surface based upon the measurement using a navigation system; and presenting the determined angle to a user.

Various embodiments are described, wherein the navigation system calculates an angle error between the determined angle and a planned resection angle of the bone and wherein presenting the determined angle to a user includes presenting the angle error to the user.

BRIEF DESCRIPTION OF THE DRAWINGS

In order to better understand various exemplary embodiments, reference is made to the accompanying drawings, wherein.

DETAILED DESCRIPTION

Figure 1A:
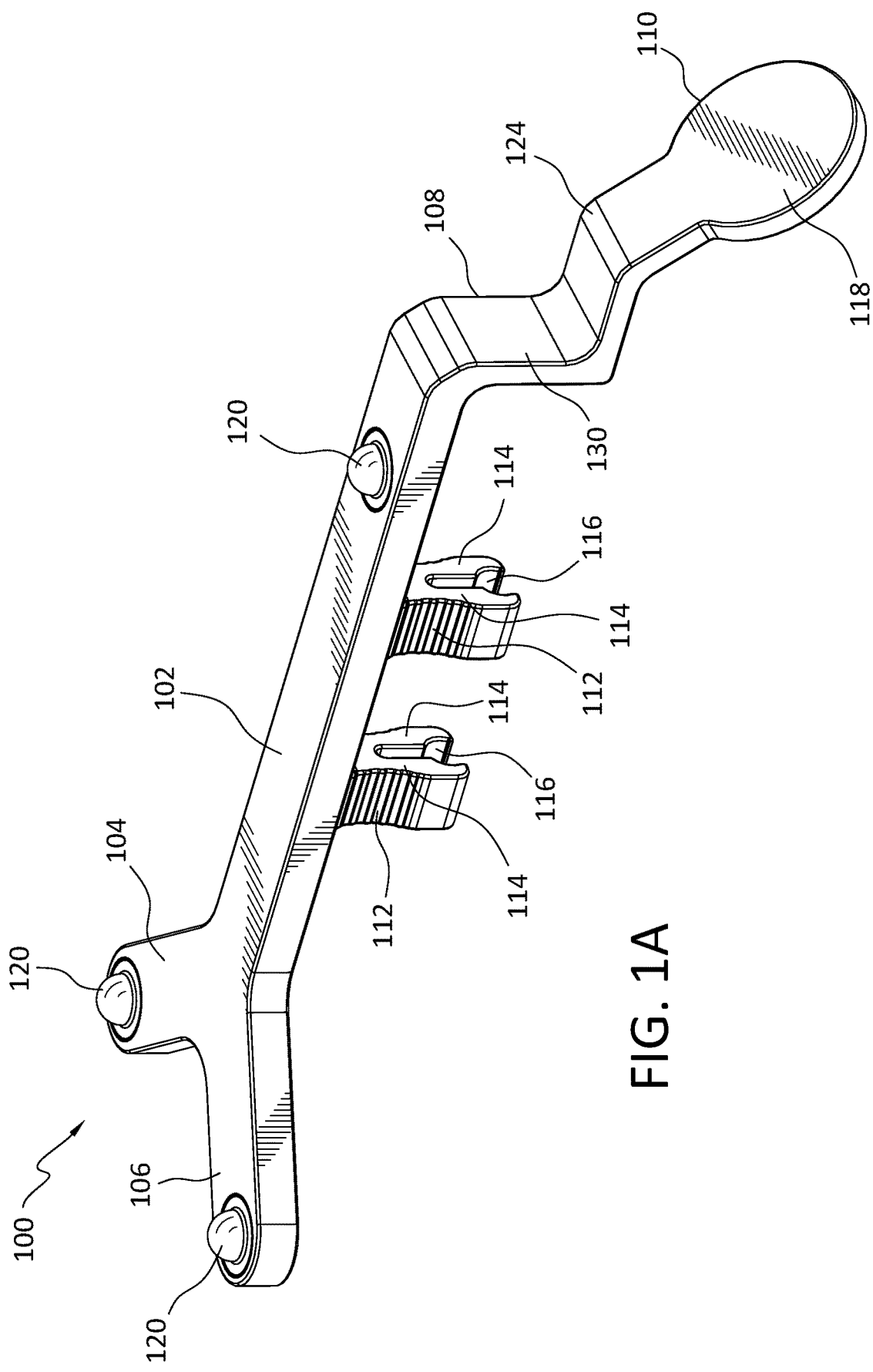
FIGS. 1A-1H illustrate an embodiment of the verification instrument.
Figure 1B:
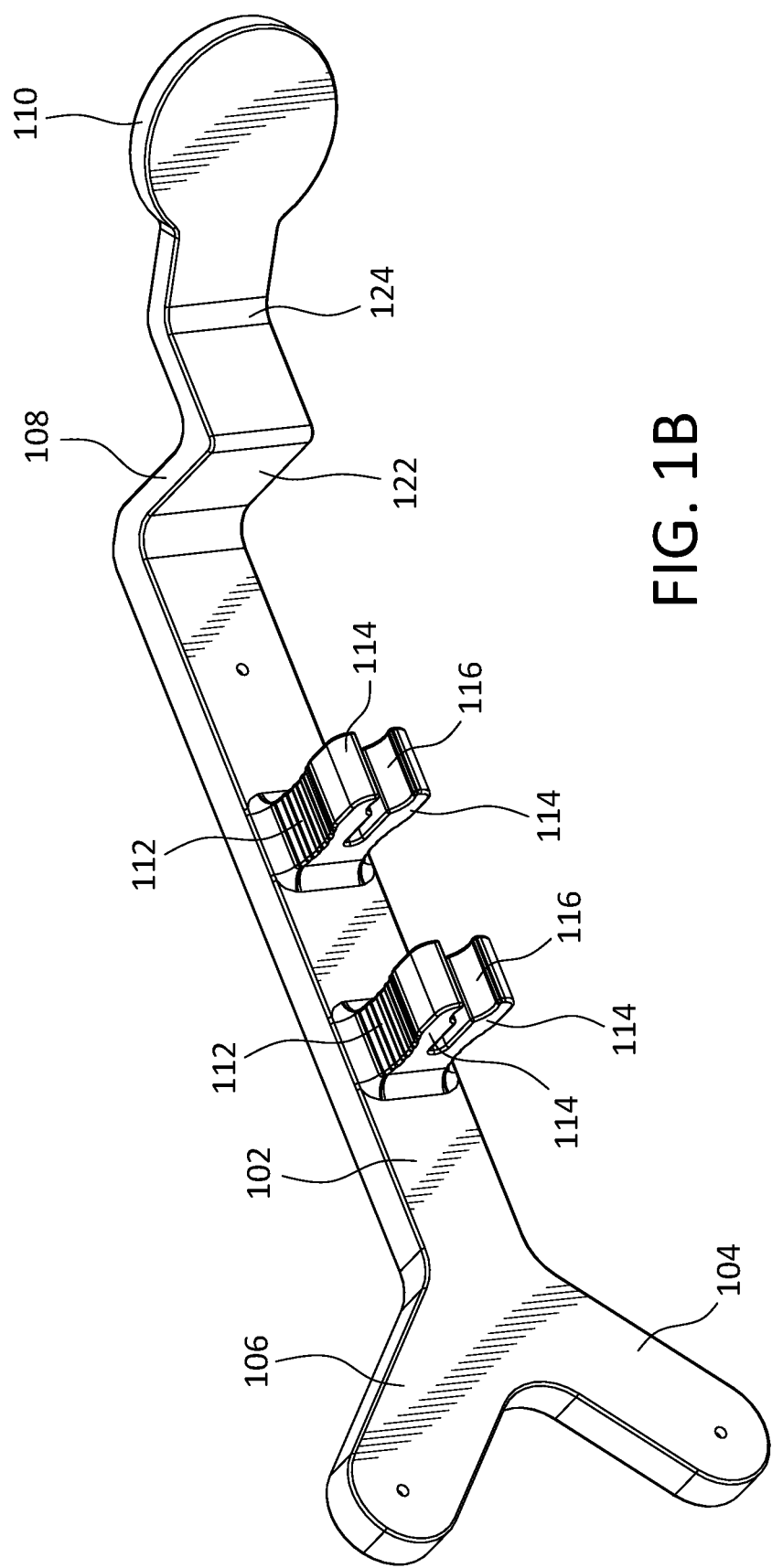
Figure 1C:
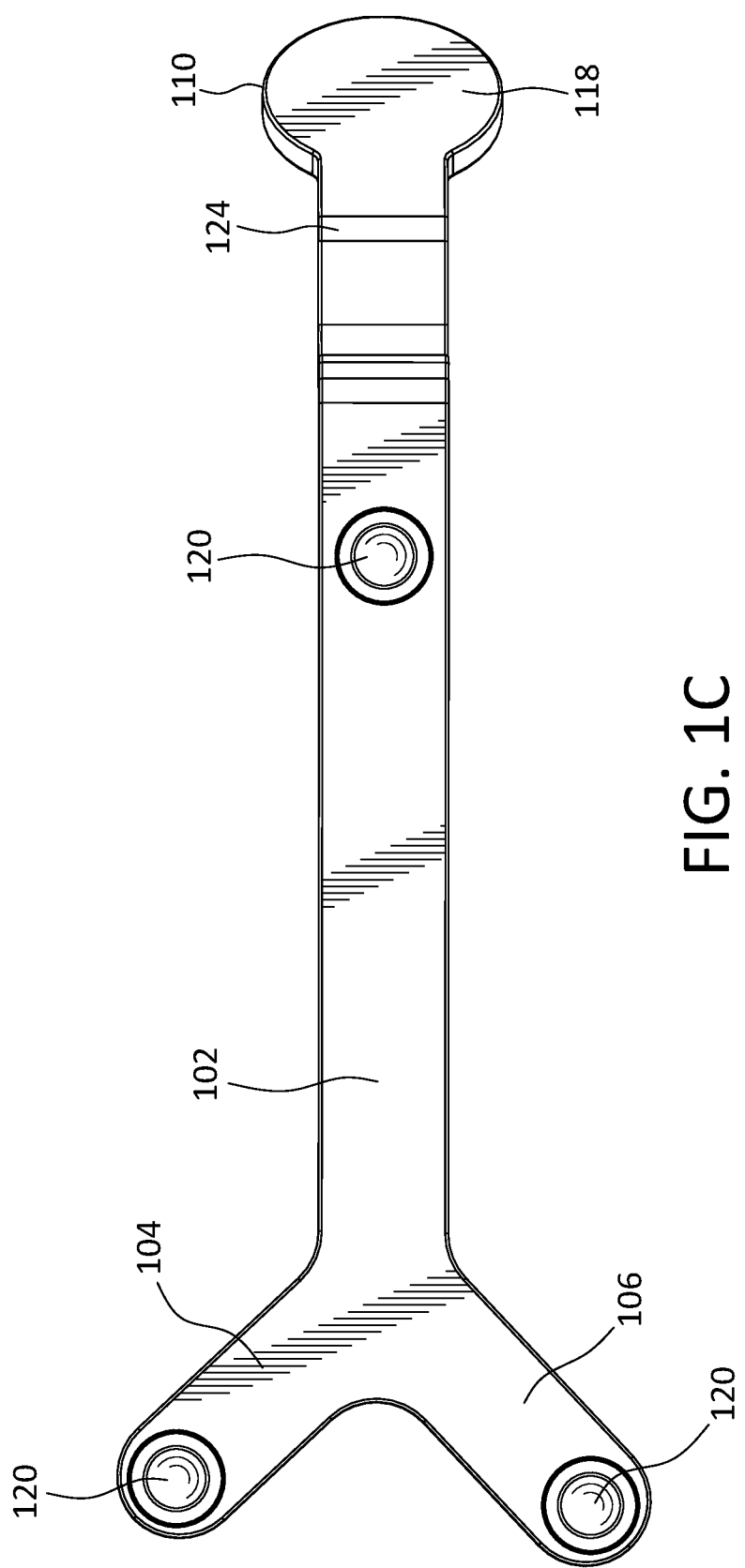
Figure 1D:
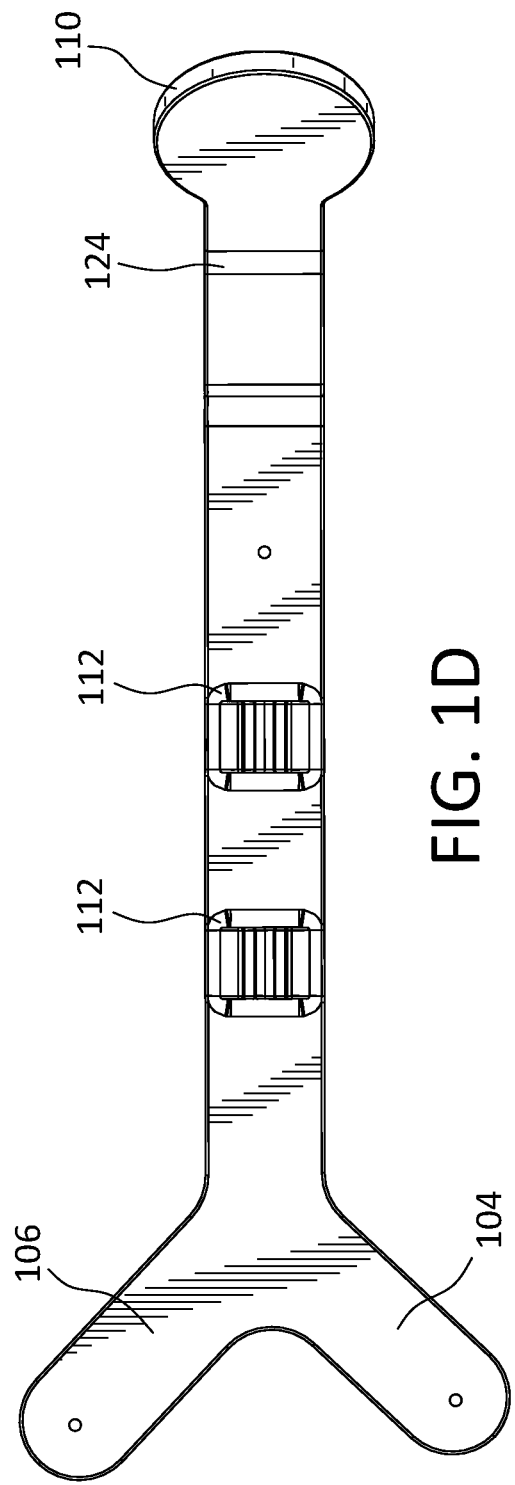
Figure 1E:
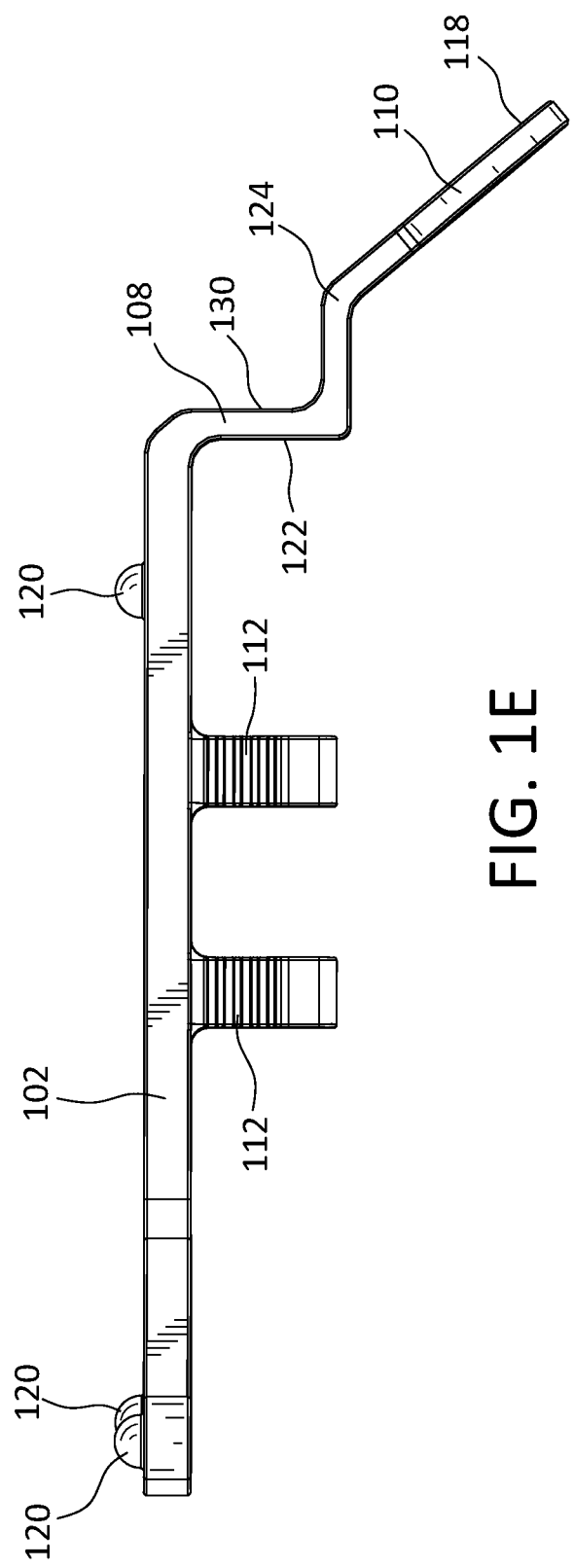
Figure 1F:
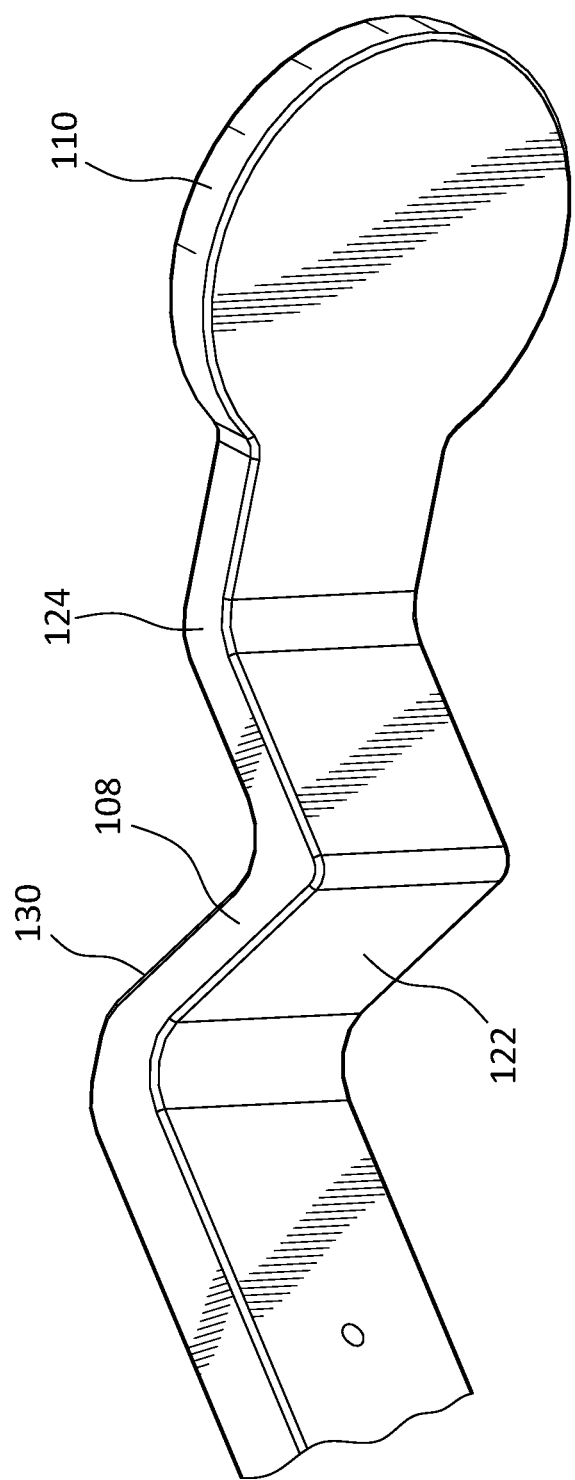
Figure 1G:
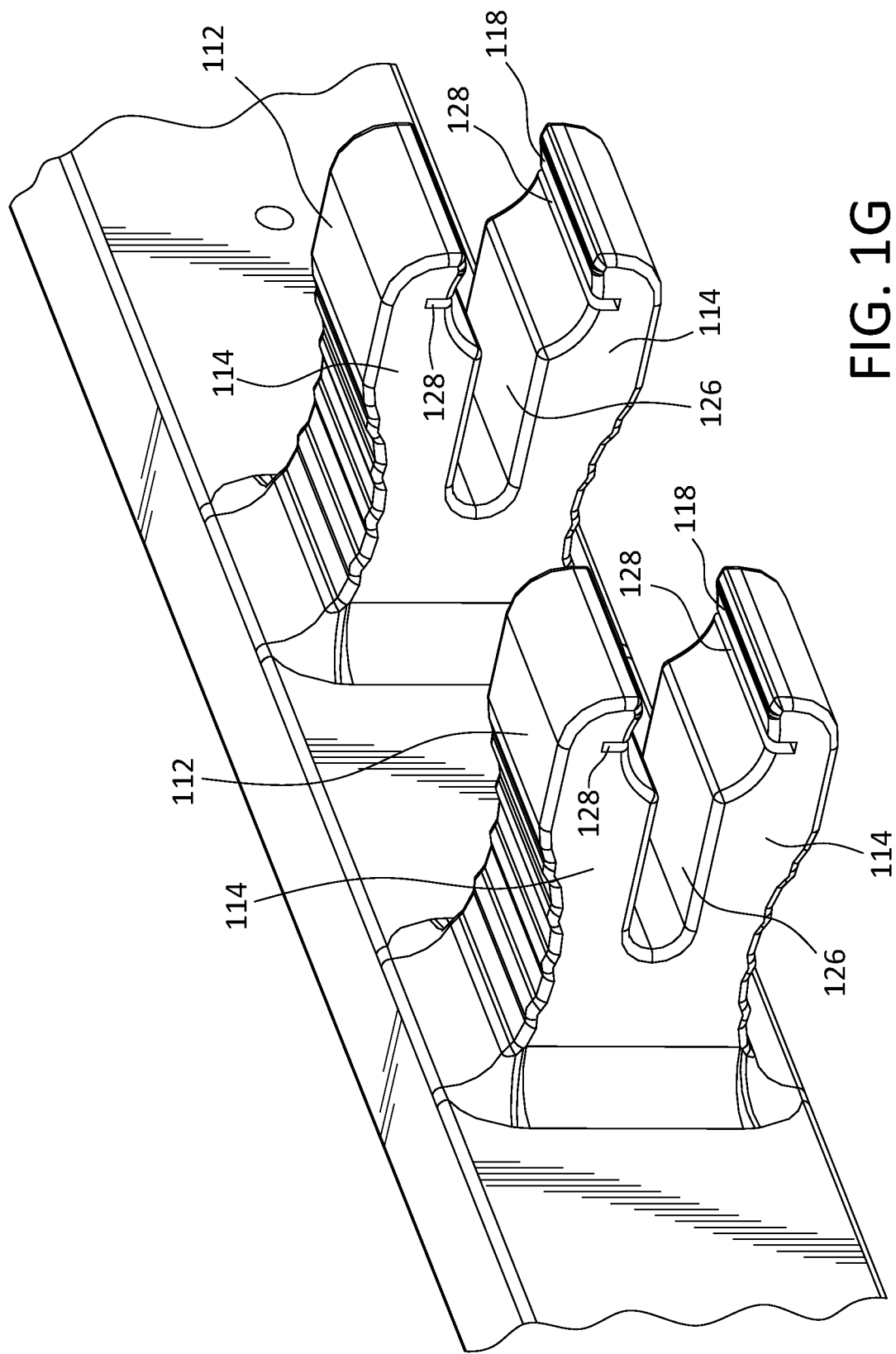
Figure 1H:
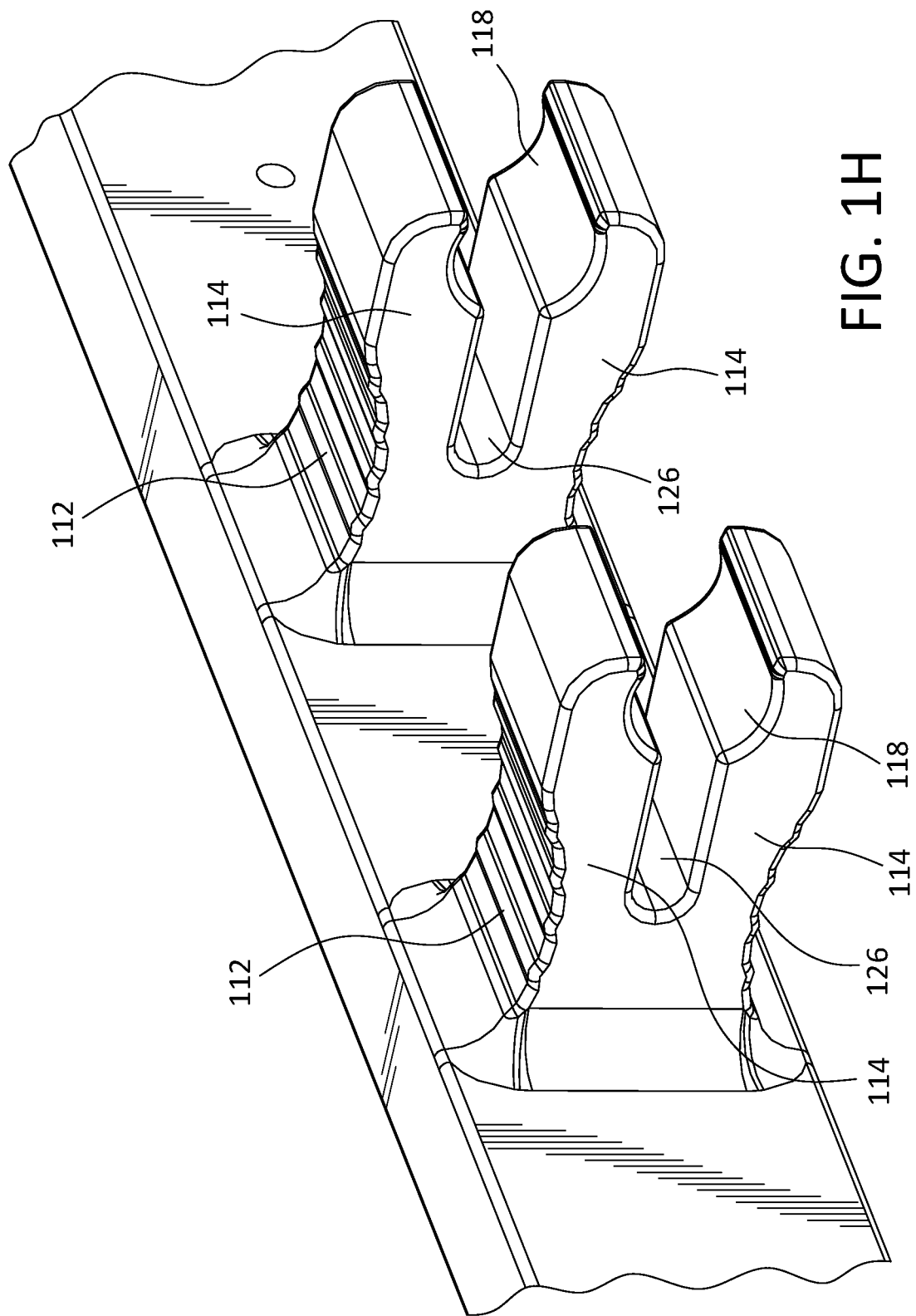

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Navigation arrays may be utilized in any of a variety of procedures requiring surgical navigation of one or more instruments and/or portions of patient anatomy. The navigation arrays may be coupled to instruments used in a procedure and/or to portions of a patient's anatomy. Further, the disclosed navigation arrays may include navigation elements to aid in positioning the navigation arrays in an optimum position that allows for detection by a surgical navigation system and positions the arrays in a manner that avoids interference with the surgical procedure (e.g., at locations where the array will not impede access to a surgical site, use of a surgical tool, etc.). The navigation elements may include reflective markers, active LEDs, electromagnetic trackers made of coils, combination of inertial sensors, ultrasonic sensors, RFID sensors, etc. The navigation system may then detect the location of the navigation elements using various techniques. The navigation elements described in the embodiments below will be reflective markers that may be detected by a camera system to determine the location of the markers and hence the navigation array. The navigation system may also illuminate the navigation array with visible light or light outside the visible range. But, other types of navigation elements may be used in the embodiments described below along with their associated navigation detection sensors.

The data from the navigation arrays may be superimposed on pre-operative images in order to assist the surgeon in performing various surgical tasks, such as cuts, drilling, reaming, etc. A navigation array attached to the patient's anatomy may provide the needed reference system to allow the locations of the navigation arrays to be properly located relative to pre-operative images.

An embodiment of a verification instrument for use in a total shoulder arthroplasty (TSA) will now be described. Such TSA may use a robot to assist in the surgery, but the verification instrument may be used with or without a robot. It noted that the verification instrument may be used in other types of surgical procedures. In such cases, the verification instrument may be sized and shaped according to the specific application.

It is typical to calibrate linear end-effector (reamer, drill) that would be mounted on a tracked handpiece for robotic surgery. Furthermore, different linear instruments could be used during the surgery and it is important for the robotic system to know and to check which end-effector is used at which step of the surgical procedure. Finally, the verification instrument may also be used by the user to check the accuracy of the resection performed with the robotic system.

The verification instrument may be used to detect any discrepancies between the theoretical position of the end effector relative to the handpiece array. The verification instrument acts to verify the position of the end effector which helps to increase accuracy during the procedure. For example, saw blades, reamers, drills, etc. may be used as end-effectors during a surgical procedure. The precise location of the end-effector relative to the handpiece (e.g., rotary driver or saw driver) is important to know in order to carry out precise cutting, drilling, reaming, etc. steps. The verification instrument may be mounted on the end-effector. A section on the verification instrument will be in contact with the tip of the end-effector. The verification instrument may rotate around the main axis of the end-effector. The verification instrument's navigation array and the handpiece navigation array positions are tracked by an infra-red camera in the navigation system. The exact position and orientation of the end-effector relative to the handpiece array may then be computed by software in the navigation system, and then compared to the theoretical positions and orientations.

The verification instrument may also facilitate the automated software identification of end-effectors. It is important that the surgical system software knows which end-effector is mounted on the handpiece at each step of the robotic surgical procedure. Because the length of the end-effectors (blades, reamers, and drills) will vary (e.g., in 3 to 5 mm increments), determining the length of the end-effector will allow the surgical system software to identify which instrument is mounted on the handpiece (i.e., end-effector 1 with total length of 120 mm, end-effector 2 with total length of 125 mm, etc.). The navigation camera will see the verification instrument and handpiece navigation arrays at the same time, and the navigation software will compute the distance and orientation between the navigation arrays and determine which end-effector is mounted on the handpiece.

The verification instrument may also be a plane tool to check the accuracy of resections, e.g., a humeral resection in the case of a TSA. When a bone is resected, the surgeon would like to check the accuracy of the resection once performed. A portion of the verification instrument such as a resection measurement portion may be placed on the resected surface. The navigation system can then detect the navigation elements on the verification instrument and calculate the angle and location of the resection based upon the known size and geometry of the verification instrument and the location of the bone based upon detecting the location of navigation elements on a bone navigation array. The measured resection values can then be compared to the planned resection values and distance and angle errors may be displayed to the surgeon. Further, the measurements taken using the verification instrument may also be used to assist in calibrating the navigation and measurement system or to correct the calibration used in the navigation and measurement system.

FIGS. 1A-1H illustrate an embodiment of the verification instrument. The verification instrument is generally Y-shaped including a body 102 and extensions 104 and 106 that form the Y-shape. The verification instrument 100 include three navigation elements 120. One navigation element 120 is on the body 102 and one navigation element 120 is near the end of each the extensions 104 and 106. Typically at least three navigation element 120 are needed in order for the navigation system to accurately calculate the position and orientation of the navigation elements 120. More navigation elements may be used as well, which would provide increased ability of the navigation system to see at least three of the navigation elements 120. It is noted that the verification instrument 100 may take other shapes such as a T-shape or any other shape that provides the needed spacing of the navigation elements 120 so that the navigation system can accurately determine the positions of the navigation elements 120 and hence the location and orientation of the verification instrument 100.

The verification instrument 100 includes clips 112 that are configured to attached to an end-effector. The clips 112 extend from the body 102. The clips 112 may include arms 114 with a slot 126 in between. The exterior surface of the arms are textured that provides a visual cue for the user to hold the verification instrument with their fingers, especially when used as a plane checker to check the resection accuracy. A gripping surface 116 is located near the end of the arms 114. The griping surface 116 is shaped to conform to the shape of an end-effector. In this example, the gripping surface 116 may be semi-cylindrical in order to grip a cylindrical portion of an end-effector. The gripping portion may also be shaped to grip other shapes of end-effectors such as for example a flat saw blade. Alternatively, the gripping surface 116 may also include a slot 128 (see FIG. 1H) in its surface that accepts a flat saw blade. The embodiment of FIG. 1H could be attached to a cylindrical portion of an end-effector or to a flat end-effector such as a saw blade. Further, in the case of a cylindrical end-effector, the verification instrument 100 may be rotated around the end-effector to position the verification instrument 110 in the field of view of a navigation system camera or to be rotated by the user to allow the navigation system to track the location of the navigation tool 100 and calculate the location of the end-effector more precisely.

The arms 114 are made of a flexible material and are designed to allow for the verification instrument 100 to be securely and accurately affixed to the end-effector, while allowing the verification instrument 100 to be easily removed from the end-effector. The verification instrument 100 is shown as having two clips 112. These clips have colinear openings defined by the gripping surface 118. This allows for proper alignment of the verification instrument with an elongated end-effector and is important as it allows for the orientation of the end-effector to be accurately determined. Alternatively more clips may be used. Also, only one clip may be used, but it would have a width large enough to ensure that the verification instrument reliably and repeatably properly aligns with the end-effector when attached.

The verification instrument 100 also includes a length measurement section 108. The length measurement section 108 extends substantially perpendicular from one end of the body 102. The length measurement section 108 has a measurement surface 122 facing the clips 112. As the precise location of the measurement surface 122 is known relative to the navigation elements 120, the length measurement surface 122 may be used to locate the end of the end-effector. This may be done by attaching the verification instrument 100 to the end-effector and sliding the verification instrument 100 along the end-effector, if needed, so that the measurement surface 122 is in contact with the tip of the end-effector. This allows for the precise location of the end-effector to be determined by the navigation system. It is especially important to know the location of the tip of the end-effector as it will resect bone or other tissue, and this needs to be done correctly and precisely. Further, this allows for the navigation system to determine the length of the end-effector. If each of the different end-effectors that may be used have a different known length, then the measured length of the end-effector may be used to identify the specific end-effector that is coupled to the handpiece. While the length measurement section 108 is shown as substantially perpendicular to the body 102, it may be at another angle.

The verification instrument 100 may also include a resection measurement section 110. The resection measurement section 110 is shown as round, but may be other shapes as well. The resection measurement section 110 is connected to an end of the length measurement section 108 by a connector 124. The connector 124 is shaped to place the resection measurement section 110 at a known angle relative to the navigation elements 120. This allows the navigation system to calculate the angle, plane, and location of the resection of the bone using the verification instrument 100. The shape of the connector 124 may be selected so that the navigation elements 120 are in the view of the navigation system in order to facilitate the measurement of the angle and location of the resection. The resection measurement section 110 includes a resection measurement surface 118 that may be placed on the resected portion of the bone. The navigation system may then determine the angle and location of the resection based upon the location of the navigation elements 120. This then allows the navigation system to display to the surgeon any angle or location errors of the resection.

Alternatively, an outer surface 130 of the length measurement section 108 that is on the opposite side from the measurement surface 122 may be used as a resection surface. In this situation the verification instrument may not include the connector 124 or the separate resection measurement section 118. Instead, the outer surface 130 may be placed on the resected bone. The angle, plane, and location of the resection will be calculated as described above.

The verification instrument 100 may be manufactured of any material that provided the needed stability of the verification instrument 100 and the flexibility of the clips 112. The verification instrument 100 may be made from various plastics and molded or 3-D printed. Alternatively, the verification instrument may be made of metal. Then the navigation elements 120 may be installed on the verification instrument 100. In another embodiment, the navigation element may be directly integrated into the verification instrument design. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth.

Figure 2A:
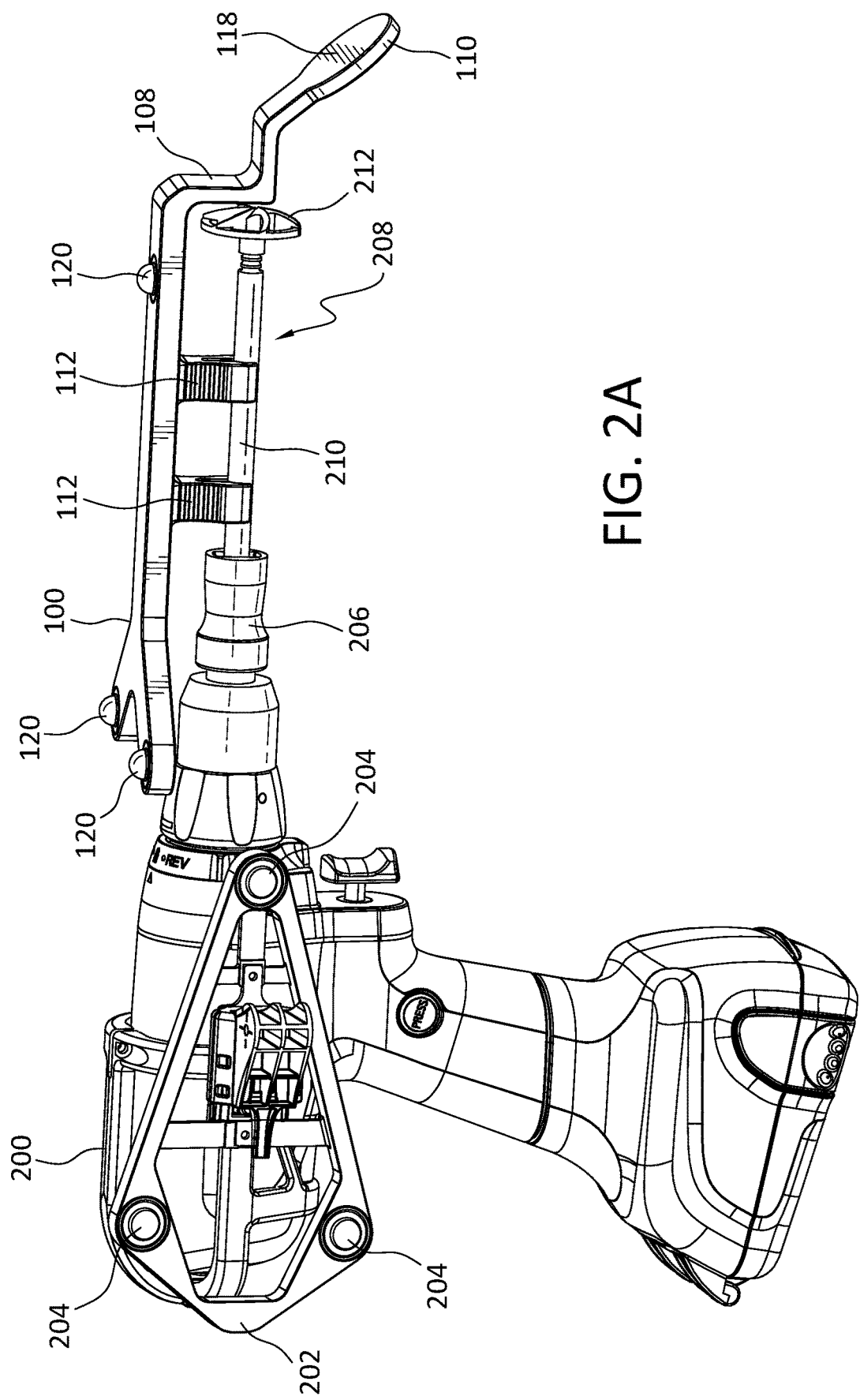
FIGS. 2A-2C illustrate the verification instrument attached to an end-effector and handpiece.
Figure 2B:
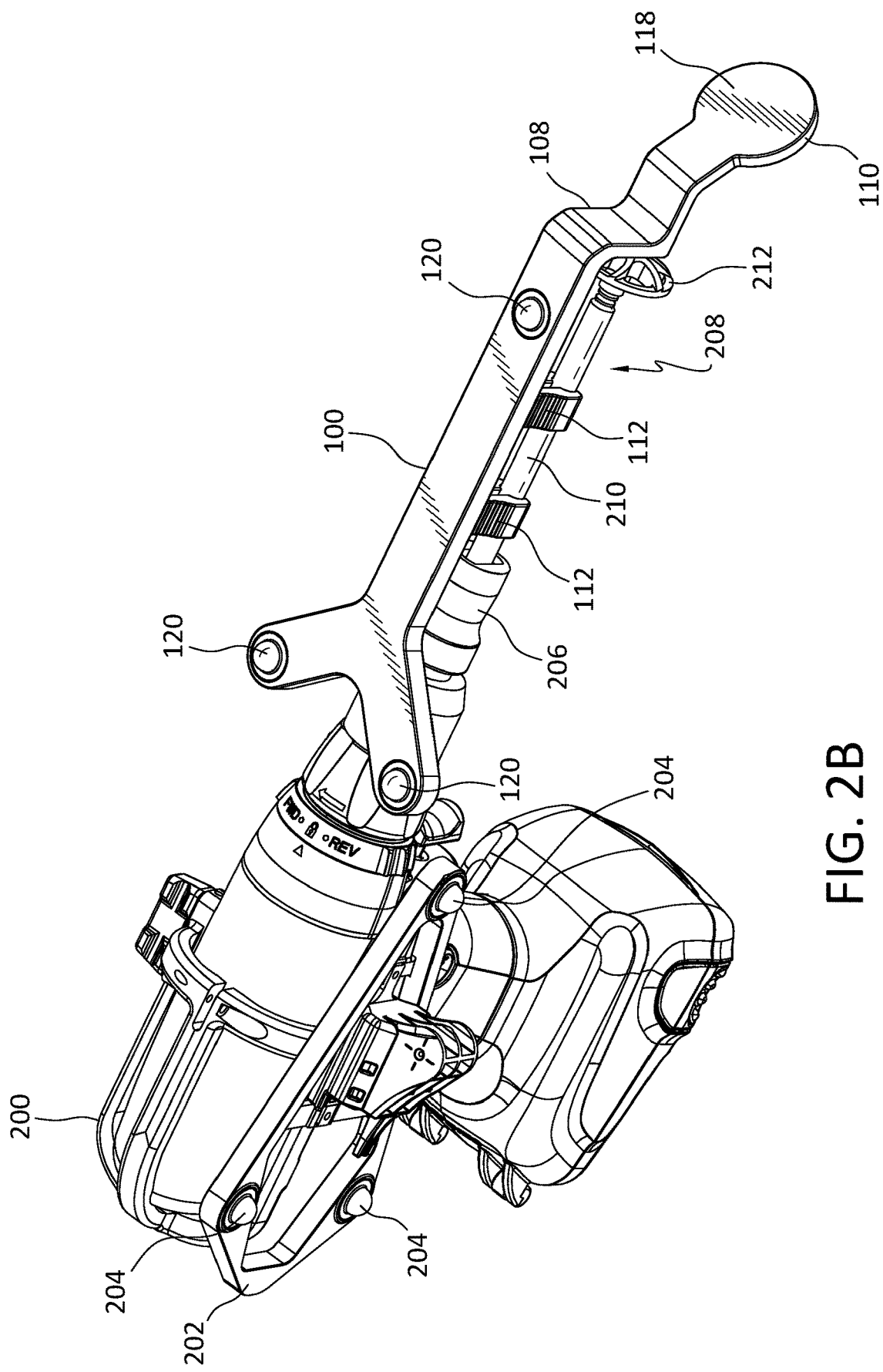
Figure 2C:
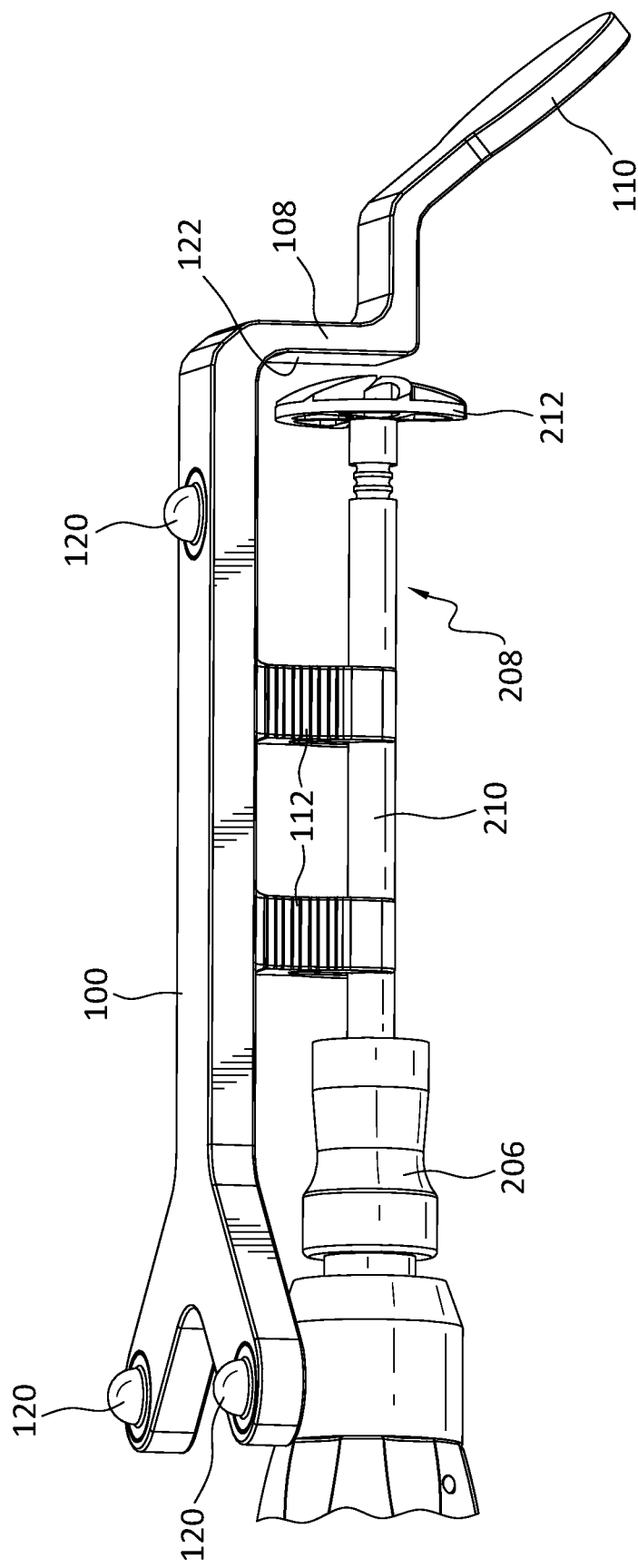

FIGS. 2A-2C illustrate the verification instrument attached to an end-effector and handpiece. A handpiece 200 is attached to end-effector 208 using a chuck 206. In this example the handpiece 200 is a drill that rotates the end-effector 208. Other types of handpieces 200 may also be used with the end-effector 208, including a saw or a burr handpiece, etc. The end-effector 208 illustrated is a reamer, but may be other types of end-effectors including drill bits, burs, saw blades, etc. The end-effector (reamer) 208 includes a shaft 210 and an attached head 212.

A navigation array 202 is attached to the handpiece 200. The navigation array 202 includes navigation elements 204 located at known locations relative to the handpiece. The exact location of the navigation elements 204 may be based upon the known mechanical mounting of the navigation array 200 on the handpiece 200. If greater accuracy of the location of the navigation array relative 200 to the handpiece 200 is needed, then a calibration procedure may be used to determine the relative locations.

The verification instrument 100 may be attached to the shaft 210 of the end-effector 208 using the clips 112. The verification instrument 100 may be slid towards the handpiece 200, if needed, in order to verify that the length measurement surface 122 is in contact with the tip of the end-effector. With the verification instrument 100 in that position, the navigation system may detect the navigation elements 120 on the verification instrument and the navigation elements 204 on the navigation array 202. The navigation system may then determine the precise location and orientation of the end-effector 208 relative to the handpiece 200. After the verification instrument 100 is removed from the end-effector 208, the navigation tool can precisely and accurately track the location and orientation of the end-effector by tracking the navigation array 202 on the handpiece 200.

Further, the navigation system can determine the length of the end-effector 208 based upon the position of the verification instrument 100 as the tip of the end-effector 208 is in contact with the length measurement surface 122. The various end-effectors 208 that may be used will be designed to have different lengths, so a measurement of the length of the end-effector 208 will allow the navigation system to identify what end-effector 208 is attached to the handpiece 200. The minimum length difference between different end-effectors 208 has to be larger than the measurement resolution of the navigation system.

Figure 3A:
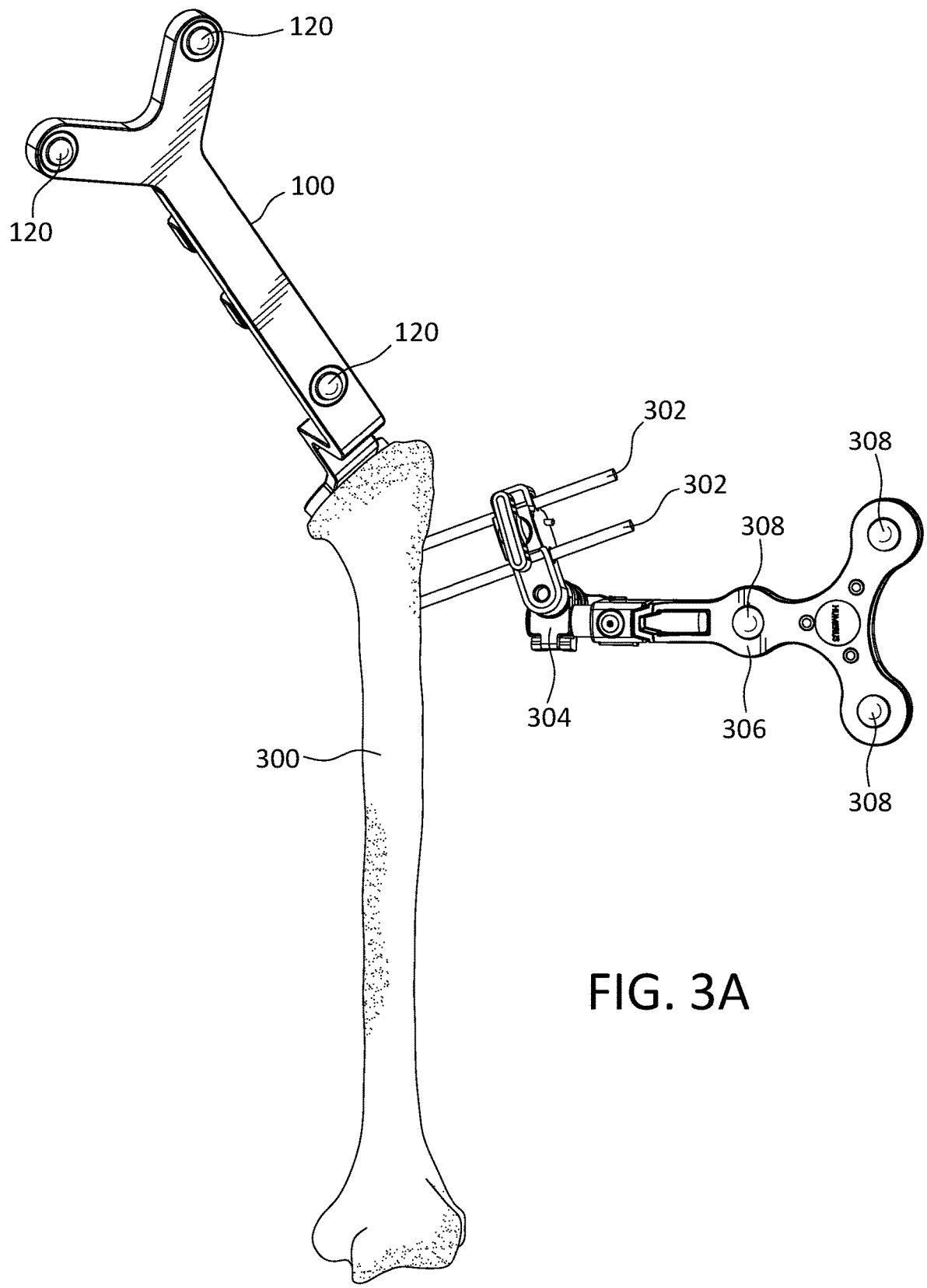
FIGS. 3A-3C illustrate different views of the verification instrument placed on a resected portion of a bone.
Figure 3B:
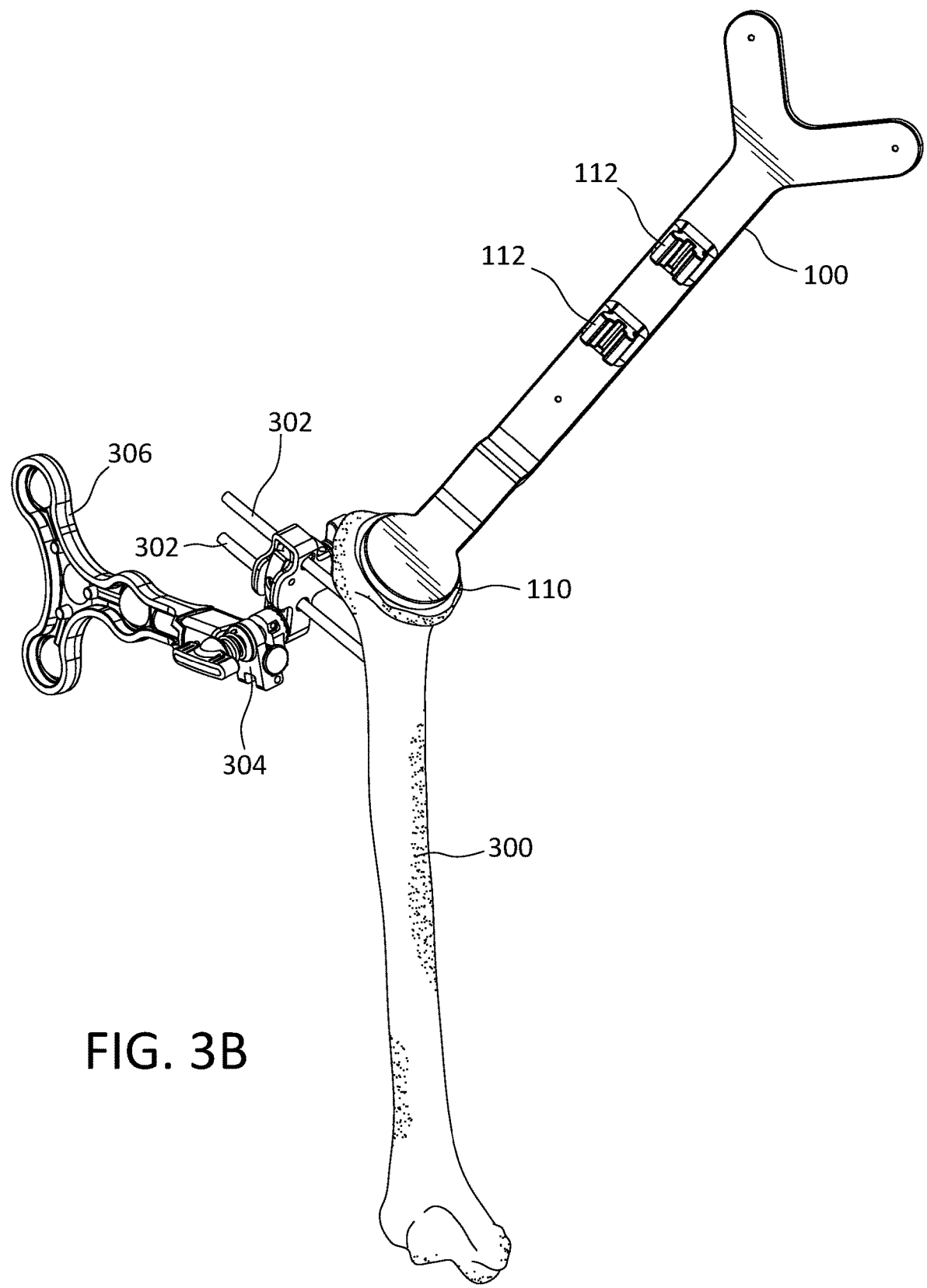
Figure 3C:
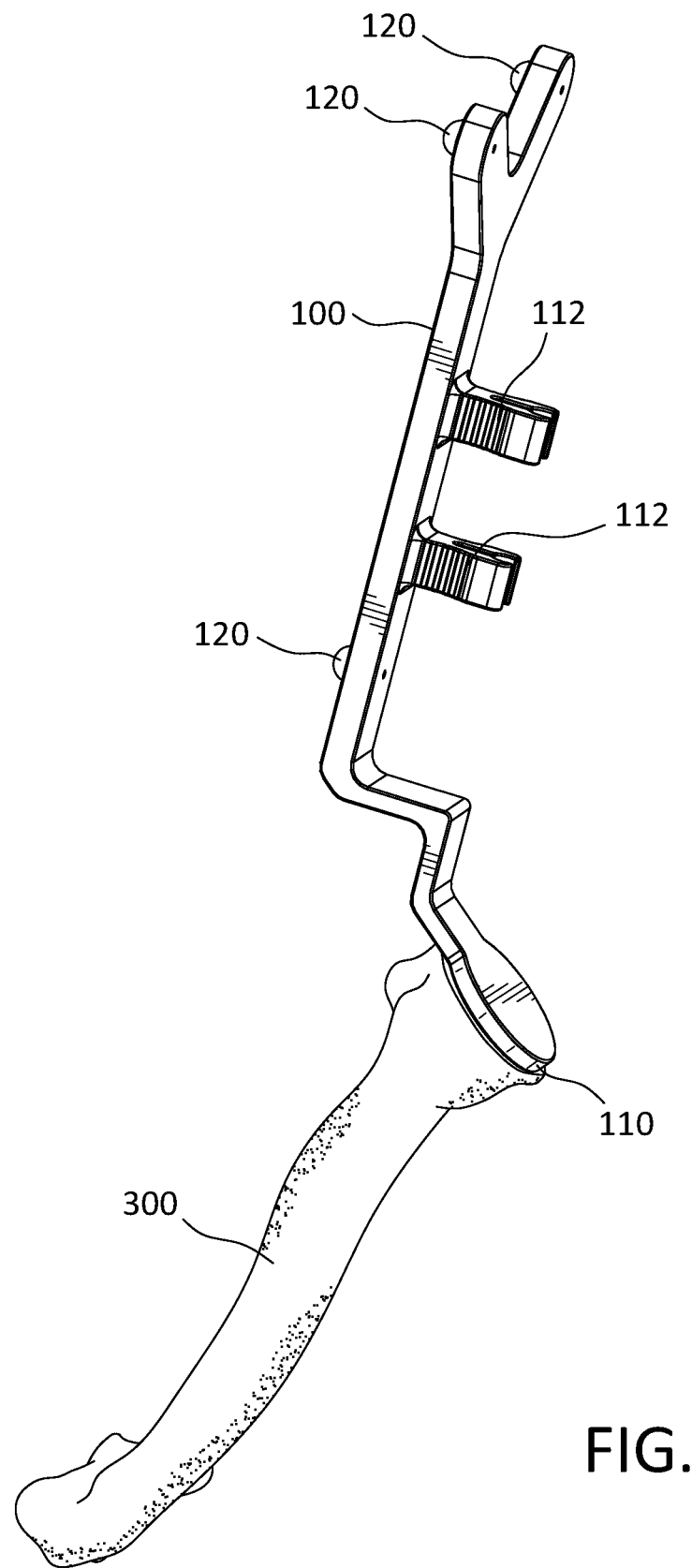

FIGS. 3A-3C illustrate different views of the verification instrument placed on a resected portion of a bone. The resection measurement surface 118 is placed in contact with the resected surface of the bone 300. Also, a navigation array 306 is fixed relative to the bone 300 using pins 302 and array clamp 304. During surgery the pins 302 are inserted in the bone 300 to be resected. Then the array clamp 304 with the attached navigation array 306 is attached to the pins 302. The array clamp 304 allows for the navigation array 304 to be oriented in various directions. The navigation array 304 is adjusted so that it is visible to the navigation system to allow for the navigation system to determine the location of the navigation array 304. After the navigation array 304 is fixed relative to the bone 300, the navigation system may measure the location and orientation of the navigation array 306 relative to the bone 300 based upon a bone navigation array attached to the bone that is detected and located by the navigation system. Then, when the verification instrument 100 is placed on the resected surface of the bone 300, the navigation system may measure the location of the verification instrument 100 using the navigation elements 120. This measurement may then be used to determine the location and angle of resection surface of the bone. These measurements may then be used to provide a measure of the error between the measured angle and location and the planned angle and location.

The following method may use the verification instrument 100 to verify the location of the tip of the end-effector. An end-effector 208 is selected and attached to the handpiece 200. The verification instrument 100 is connected to the end-effector 208 using clips 112. The verification instrument is adjusted, if need be, so that the tip of the end-effector 208 contacts the length measurement surface 120. Alternatively, the verification instrument 100 is connected to the end-effector 208 in such a way that the tip of the end-effector 208 contacts the length measurement surface 120. The navigation system is used to measure the location of the verification instrument 100. The navigation system then validates the location and orientation of the tip of the end-effector 208 relative to a navigation array 202 on the handpiece 200. This provides the navigation system a precise location of the end-effector during the surgery that may be used to provide feedback to the surgeon. Also, the navigation system may determine the length of the end-effector 208 and then based upon the determined length identify the type of end-effector 208 attached to the handpiece 200 and present that information to the surgeon.

The following method may use the verification instrument 100 to measure the angle and location of a resection surface of a bone. The surgeon places the resection measurement tool 100 on the resection surface of the bone. The navigation system is then used and the location and orientation of the verification instrument 100 is measured. The navigation system then determines the angle and location of the resection surface of the bone and calculates and presents errors in the actual angle and location of the resection surface relative to the planned resection. These errors may be presented to the surgeon. At this point if the errors associated with the resection surface are too great, the surgeon can take remedial actions.

The navigation system may be part of a surgical system used to guide the surgeon through the surgery. A robot may or may not be used in the surgery. The navigation system may include a processor, memory, user interface, network interface, and storage interconnected via one or more system buses. A camera or other sensor (depending upon the type of navigation element) is connected to the processor. The camera collects image information that may be processed by the processor to determine location of the various navigation elements and then to calculate the relative position of various elements in the view of the navigation system.

The processor may be any hardware device capable of executing instructions stored in memory or storage or otherwise processing data. As such, the processor may include a microprocessor, microcontroller, graphics processing unit (GPU), field programmable gate array (FPGA), application-specific integrated circuit (ASIC), neural network processors, machine learning processors, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The user interface may include one or more devices for enabling communication with a user as needed. For example, the user interface may include a display, a touch interface, a mouse, and/or a keyboard for receiving user commands. In some embodiments, the user interface may include a command line interface or graphical user interface that may be presented to a remote terminal via the network interface.

The network interface may include one or more devices for enabling communication with other hardware devices such as other computer networks or cameras or other sensors that are part of the navigation system. For example, the network interface may include a network interface card (NIC) configured to communicate according to the Ethernet protocol or other communications protocols, including wireless protocols. Various alternative or additional hardware or configurations for the network interface will be apparent.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. For example, the storage may store a base operating system for controlling various basic operations of the hardware. The storage may include instructions for carrying out the various measurement and calibration calculations of the navigation system described above.

It will be apparent that various information described as stored in the storage may be additionally or alternatively stored in the memory. In this respect, the memory may also be considered to constitute a "storage device" and the storage may be considered a "memory." Various other arrangements will be apparent. Further, the memory and storage may both be considered to be "non-transitory machine-readable media." As used herein, the term "non-transitory" will be understood to exclude transitory signals but to include all forms of storage, including both volatile and non-volatile memories.

When software is implemented on a processor, the combination of software and processor becomes a single specific machine. Although the various embodiments have been described in detail, it should be understood that the invention is capable of other embodiments and its details are capable of modifications in various obvious respects.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The verification instrument 100 disclosed herein may be designed to be disposed of after a single use, or it may be designed to be used multiple times. The verification instrument 100 may be reconditioned for reuse after use. Reconditioning may include any combination of the steps of disassembly of the verification instrument 100, followed by cleaning or replacement of particular pieces, and subsequent reassembly. In particular, the verification instrument 100 may be disassembled, and any number of the particular pieces or parts of the verification instrument 100 can be selectively replaced or removed in any combination. Upon cleaning and/or replacement of particular parts, the verification instrument 100 can be reassembled for subsequent use either at a reconditioning facility, or by a surgical team immediately prior to a surgical procedure. Those skilled in the art will appreciate that reconditioning of a verification instrument 100 may utilize a variety of techniques for disassembly, cleaning/replacement, and reassembly. Use of such techniques, and the resulting reconditioned verification instrument 100, are all within the scope of the present application.

The verification instrument 100 described herein may be processed before use in a surgical procedure. First, a new or used verification instrument 100 may be obtained and, if necessary, cleaned. The verification instrument 100 may then be sterilized.

In the description above, a surgeon is described as carrying out various steps and actions. Other personnel or users involved in the surgery may also carry out these steps or actions.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A verification instrument configured to verify a location of a surgical end-effector, comprising:
   a body;
   a first navigation element disposed and configured to represent a spatial location of the body;
   a first clip extending from the body and configured to clip onto a tool;
   a second clip extending from the body and configured to clip onto the tool, where the first clip includes a first opening, the second clip includes a second opening, and the first and second openings are colinear with each other; and
   a length measurement portion disposed at a first angle from the body, wherein the length measurement portion is configured to contact a tool tip in a direction that is colinear with the first opening and the second opening,
   wherein the first clip has a first arm having a first gripping surface, a second arm having a second gripping surface, the first arm and the second arm each extending away from the body in a substantially perpendicular direction, the first arm and the second arm defining a slot between them.

2. The verification instrument of claim 1, further comprising a resection measurement portion connected to a connector at a second angle from the body.

3. The verification instrument of claim 1, further comprising:
   a second navigation element disposed and configured to represent the spatial location of the body;
   wherein the body further comprises a first extension extending from the body, and a second extension extending from the body,
   the first navigation element is located at a distal end of the first extension, and
   the second navigation element is located at a distal end of the second extension.

4. The verification instrument of claim 1, wherein the first angle is substantially 90 degrees.

5. The verification instrument of claim 1, wherein
   the first gripping surface and the second gripping surface are configured to grip a cylindrical portion of the end-effector.

6. The verification instrument of claim 5, wherein the first clip comprises a first slot in the first gripping surface configured to grip a flat portion of the end-effector.

7. The verification instrument of claim 5, wherein the first arm and the second arm have a textured exterior surface.

8. The verification instrument of claim 1, wherein the second clip has a third arm and a fourth arm, the third arm and the fourth arm each extending away from the body in the substantially perpendicular direction.

9. The verification instrument of claim 1, wherein the first gripping surface is disposed at a distal end of the first arm, and the second gripping surface is disposed at a distal end of the second arm.

10. The verification instrument of claim 1, further comprising:
a resection measurement portion; and
a connector coupled between the length measurement portion and the resection measurement portion.

11. A verification instrument configured to verify the location of a surgical end-effector, comprising:
a body;
a first navigation element disposed and configured to represent a spatial location of the body;
a second navigation element, spaced apart from the first navigation element, disposed and configured to represent the spatial location of the body;
a first clip attached to the body, the first clip having a first gripping surface, and a first arm and a second arm each extending perpendicularly away from the body and configured to clip onto a tool;
a second clip attached to the body, the second clip having a second gripping surface, and a third arm and a fourth arm each extending perpendicularly away from the body and configured to clip onto the tool, wherein the first clip includes a first opening, the second clip includes a second opening, and the first opening and second openings are colinear; and
a length measurement portion disposed at a first angle from the body, wherein the length measurement portion is configured to contact a tool tip in a direction that is colinear with the first opening and the second opening.

12. The verification instrument of claim 11, wherein the first opening is defined, at least in part, by the first gripping surface, and the second opening is defined, at least in part, by the second gripping surface.

13. The verification instrument of claim 11, further comprising:
a resection measurement portion; and
a connector coupled between the length measurement portion and the resection measurement portion.

14. The verification instrument of claim 13, wherein the resection measurement portion is disposed at a second angle from the body, and the first angle and the second angle are different from each other.

15. The verification instrument of claim 13, wherein the resection measurement portion has a resection measurement surface.

16. The verification instrument of claim 11, wherein the body further comprises a first extension extending from the body, and a second extension extending from the body, wherein the first extension and the second extension are coplanar with the body.

17. The verification instrument of claim 16, wherein the length measurement portion has a measurement surface and a resection surface opposite the measurement surface.

18. The verification instrument of claim 11, wherein the length measurement portion has a measurement surface.

19. The verification instrument of claim 18, wherein the length measurement portion is disposed at a first end of the body, the first extension is disposed at a second end of the body, and the second extension is disposed at the second end of the body.

20. The verification instrument of claim 11, wherein the first angle is substantially 90 degrees.

* * * * *